(12) United States Patent
Wiltshire et al.

(10) Patent No.: US 9,421,350 B2
(45) Date of Patent: Aug. 23, 2016

(54) WOUND MANAGEMENT DEVICE

(75) Inventors: Neil Wiltshire, Birmingham (GB); Eric Davison, Birmingham (GB)

(73) Assignee: Salts Healthcare Limited, Aston, Birmingham, West Midlands (GB)

( * ) Notice: Subject to any disclaimer, the term of this patent is extended or adjusted under 35 U.S.C. 154(b) by 522 days.

(21) Appl. No.: 13/813,230

(22) PCT Filed: Jul. 29, 2011

(86) PCT No.: PCT/GB2011/051447
§ 371 (c)(1),
(2), (4) Date: May 13, 2013

(87) PCT Pub. No.: WO2012/013986
PCT Pub. Date: Feb. 2, 2012

(65) Prior Publication Data
US 2013/0231619 A1    Sep. 5, 2013

(30) Foreign Application Priority Data

Jul. 30, 2010   (GB) ................................. 1012846.0

(51) Int. Cl.
| A61M 35/00 | (2006.01) |
| A61F 13/02 | (2006.01) |
| A61J 1/10 | (2006.01) |
| A61J 1/14 | (2006.01) |
| A61F 13/00 | (2006.01) |
| A61M 1/00 | (2006.01) |
| A61M 27/00 | (2006.01) |

(52) U.S. Cl.
CPC .......... *A61M 35/00* (2013.01); *A61F 13/00068* (2013.01); *A61F 13/02* (2013.01); *A61M 1/0023* (2013.01); *A61M 1/0086* (2014.02); *A61M 1/0088* (2013.01); *A61F 2013/00412* (2013.01); *A61J 1/10* (2013.01); *A61J 1/14* (2013.01); *A61J 1/1475* (2013.01); *A61M 1/0058* (2013.01); *A61M 1/0084* (2013.01); *A61M 27/00* (2013.01)

(58) Field of Classification Search
CPC .................. A61M 1/0086; A61M 2039/0235; A61M 2039/0264
See application file for complete search history.

(56) References Cited

U.S. PATENT DOCUMENTS

| 4,876,788 | A | * | 10/1989 | Steer | ..................... A61F 5/4404 222/572 |
| 2005/0251144 | A1 | * | 11/2005 | Wilson et al. | ................... 606/73 |
| 2006/0079852 | A1 | | 4/2006 | Bubb et al. | |
| 2008/0119802 | A1 | | 5/2008 | Riesinger | |

FOREIGN PATENT DOCUMENTS

| EP | 0117714 | 7/1989 |
| WO | 2005070480 | 5/2008 |
| WO | 2008131896 A1 | 11/2008 |
| WO | 2009088757 A1 | 7/2009 |
| WO | 2009143932 A1 | 12/2009 |

* cited by examiner

*Primary Examiner* — Tatyana Zalukaeva
*Assistant Examiner* — Kai Weng
(74) *Attorney, Agent, or Firm* — Boyle Fredrickson, S.C.

(57) ABSTRACT

A wound management device comprising at least one wall element of flexible sheet material, the device being securable to skin around a wound site to define a space wherein the wound is accessible; and a connector element held to the at least one wall element and affording at least one passage for external communication with the space; wherein the connector element includes at least one formation through which the or a passage extends, for engagement by a member for fluid supply to or removal from the space.

9 Claims, 7 Drawing Sheets

WOUND MANAGEMENT DEVICE

DESCRIPTION OF INVENTION

This invention relates to a wound management device.

Treatment of wounds can involve the use of dressings which fulfil the basic functions of covering a wound to keep it clean and protect it during healing. It may also be required to facilitate the delivery of one or more substances to the wound site and/or the removal of one or more substances from the site. For example, fluids such as liquids or gases may be supplied to or carried away from the wound site. Liquid fluids such as irrigation or cleansing agents, e.g. saline, or gases such as oxygen for aeration of the wound site may be supplied thereto. After use such fluids, in addition to wound exudates, may be conducted away from the wound site. Wound management devices, which sometimes are referred to as wound pouches, provide for such handling of fluids.

Wound management devices are also used for managing exudates from fistulas. In referring to the present invention as a wound management device, it is to be understood that it will find utility for such other purposes, where similar or analogous requirements may arise.

When a wound management device is to be used for the supply to and/or removal from a wound site of one or more fluids, it must provide for the connection of one or more fluid conduits, such as flexible tubing, to the device in such a way as to communicate with the wound site to which the device is applied. To this end it has been usual to provide a wound management device with an entry portion provided with, or able to receive, at least one element affording a through-passage by which fluid can enter or leave a space defined by the device, for access to the wound.

The present invention addresses requirements for a wound management device to be easy to use and versatile. Particular features and advantages of the invention in these respects will be pointed out hereafter.

According to one aspect of the invention, we provide a wound management device comprising at least one wall element of flexible sheet material, the device being securable to skin around a wound site, to define a space wherein the wound is accessible; and a connector element held to the at least one wall element and affording at least one passage for external communication with the space; wherein the connector element includes at least one formation through which the or a passage extends for engagement by a member for fluid supply to or removal from the space.

According to another aspect of the invention, we provide a wound management device, comprising first and second wall elements of flexible sheet material, secured to one another to define a space therebetween; a first one of said wall elements being adapted for adhesive securement to skin around a wound site, and provided or able to be provided with an opening for access between the wound site and the space between the wall elements; and a connector element held to the wall elements and affording at least one passage for external communication with the space between the wall elements; wherein the connector element includes at least one formation for engagement by a member for fluid supply to or removal from the space.

Preferably the at least one formation comprises a tubular spigot through which the respective passage extends.

The connector element may comprise a body secured to the wall elements by being received between respective portions, e.g. neck portions, thereof; it may be held therein by adhesive or by any other suitable method, e.g. plastics welding. Alternatively, a connector element body may be secured to one of the wall elements.

The connector element may afford a plurality of passages extending through the connector element to communicate with the space between the wall elements, and more than one of such passages may be provided with a formation as aforesaid. At least one of the passages may have two formations such as spigots, respectively extending into the space between the walls of the device and to the exterior of the device.

The provision of a spigot extending into the interior space between the wall elements of the device enables the fitting of an interior tube or other extension member within the management device, for delivery of fluid to or removal of fluid from the vicinity of a wound to which the management device has been applied.

In the case of a connector element affording a plurality of passages, such passages may be of similar or different sizes to one another. One passage may be intended for use as a drainage passage and typically may be of larger size than the others, and may be provided only with an exterior spigot.

In a wound management device in accordance with the invention, the provision of a connector element with at least one formation such as a spigot renders the connection or disconnection of a fluid supply or removal tube thereto extremely quick and simple, requiring a minimum of disturbance to the wound.

The invention will now be described by way of example with reference to the accompanying drawings, of which:

FIG. 4, comprising 21 thumbnail views, 4.1-4.21, illustrates the successive stages of use of a wound management device in accordance with the invention.

Figure 1:
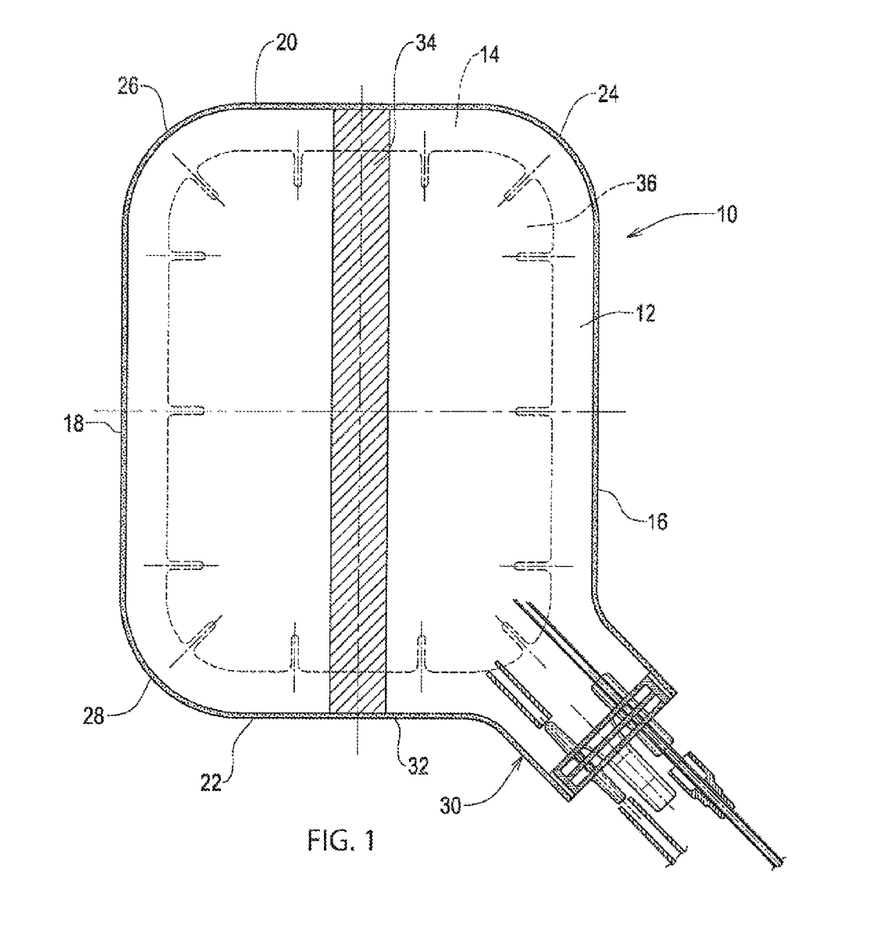
FIG. 1 is a plan view of a wound management device in accordance with the invention.
Figure 2:
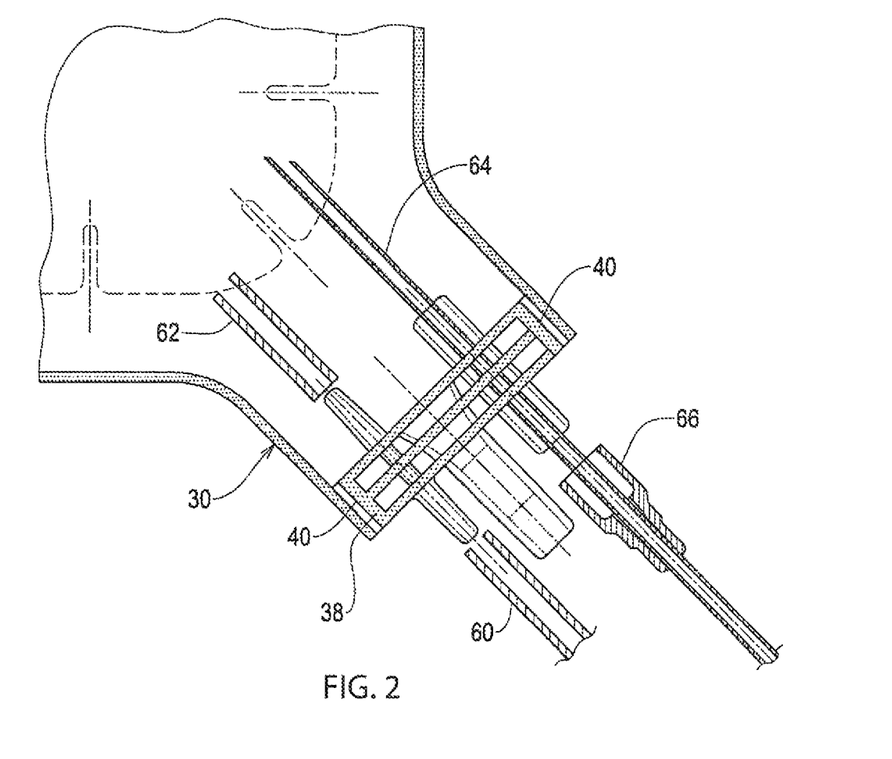
FIG. 2 is an enlargement of part of the device of FIG. 1.
Figure 3:
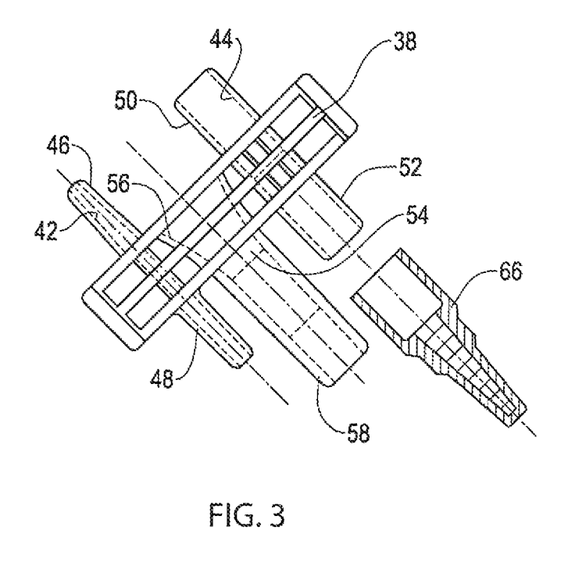
FIG. 3 shows, in isolation, a connector element of the device of FIGS. 1 and 2.
Figure 41:
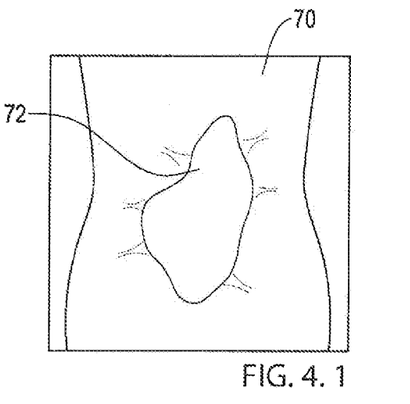
Figure 42:
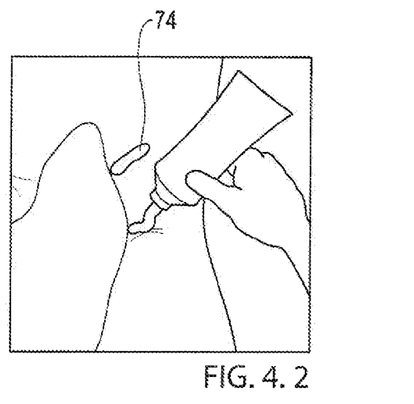
Figure 43:
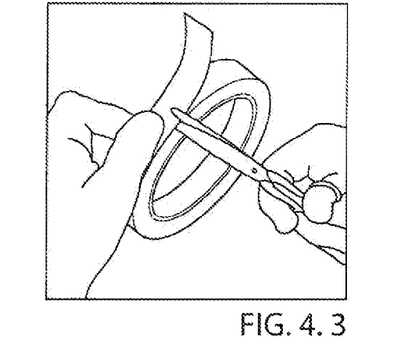
Figure 44:
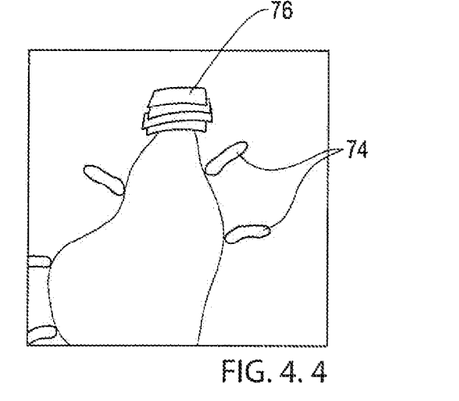
Figure 45:
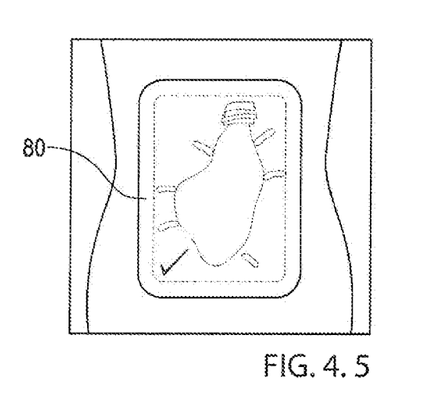
Figure 46:
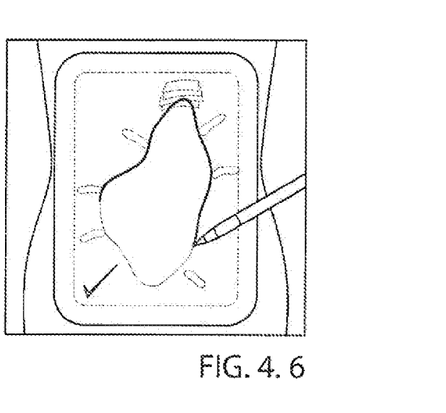
Figure 47:
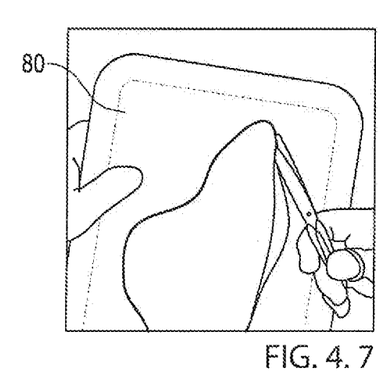
Figure 48:
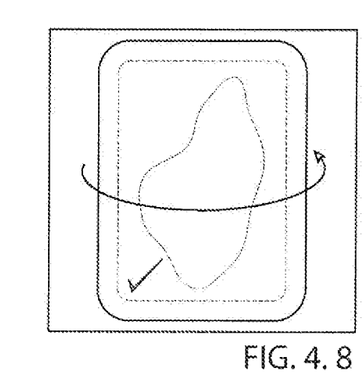
Figure 49:
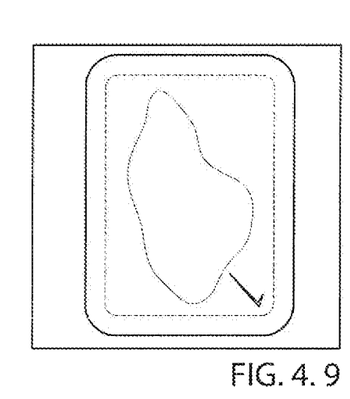
Figure 410:
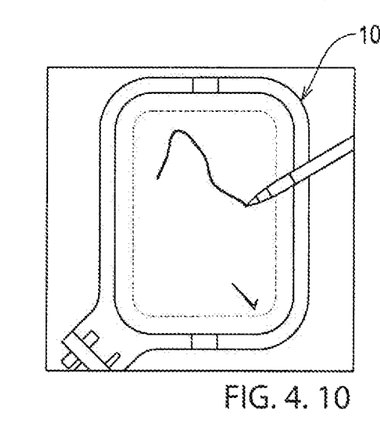
Figure 411:
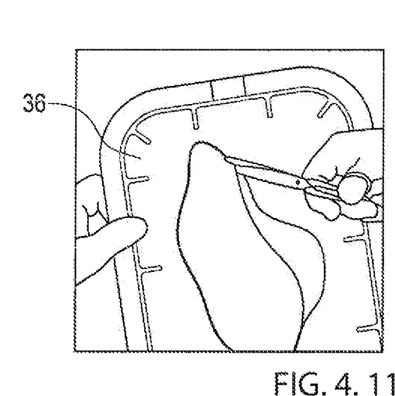
Figure 412:
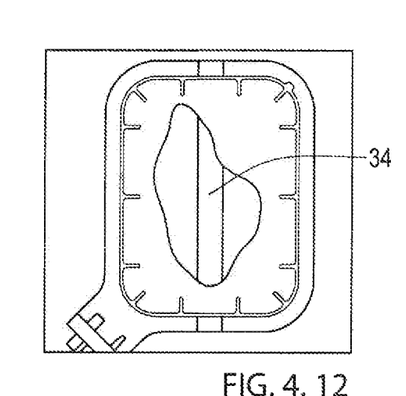
Figure 413:
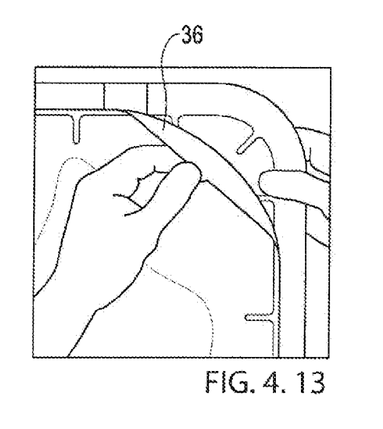

Referring firstly to FIGS. 1 to 3 of the drawings, these show a wound management device which is generally of rectangular shape, having three rounded corners and, at the fourth corner, a neck portion provided with a connector element, described hereafter in greater detail. It will be appreciated that although the illustrated device is generally rectangular in shape, and will be adapted as described hereafter to suit the shape of the wound with which it is to be used, management devices of other shapes, and in a range of different sizes, may be constructed in accordance with the invention.

The wound management device, indicated generally at 10 in FIG. 1, comprises two wall elements 12, 14 of flexible sheet material, secured together in face to face relationship and each of the above-described shape having opposite, parallel, longer edges 16, 18 and opposite parallel shorter edges 20, 22, with three arcuate corners 24, 26, 28 and at the other corner a neck portion 30 extending away from the rectangle. The wall elements 12, 14 are of a suitable plastics material and secured together by a peripheral welded joint 32 providing a fluid-tight connection, except at the free end of the neck portion 30 which is open to receive the connector element described hereafter.

The wall element 12 uppermost in FIGS. 1 and 2 is provided with an openable and re-sealable access strip 34 which conveniently may be of the configuration commonly known as a "zip-lock". This comprises respective formations of flexible plastics material provided along adjacent opposed edges of an opening, the formations including portions which in cross-section transverse to the opening have one or more undercut parts and complementary parts engageable in the undercut parts by deformation of the flexible plastics material when force is applied thereto. They are able to engage sufficiently closely to provide a substantially fluid-tight connection between the edges of the opening, and yet to be pulled apart to enable the edges of the opening to be moved away from one another for access therebetween. A slider may engage the complementary parts of the opposed edges and be arranged to cause them to be separated when it is slid in one direction therealong and engaged when slid in the opposite direction. Alternatively, an openable and resealable strip utilising an adhesive may be employed.

The wall element 14 which is underneath the wall element 12 in the view shown in FIG. 1 is provided with an element 36 of adhesive material. This is fixed to the surface of the element 14 remote from the element 12, and is provided with an adhesive able to secure the device to the skin of a patient surrounding a wound to which the device is to be applied, in the manner described hereafter. Before being used to apply the wound management device to a wound, the skin-adhesive surface of the adhesive part 36, e.g. provided with a hydrocolloid adhesive, will be covered with a removable protective release sheet.

For providing communication with the space between the wall elements 12, 14 and thereby with a wound to which the device is applied, a connector element 38 is provided in the neck portion 30. The connector element 38 is of a suitable plastics material, e.g. an injection moulding. In cross-sectional shape it is somewhat lenticular, tapering down to thin opposite edges at 40 adjacent the welded edge portions of the wall elements 12, 14, and possibly with a parallel-walled portion therebetween with sufficient thickness to accommodate the passages described hereafter. It is secured in the neck portion 30 of the device, e.g. by welding or use of a suitable adhesive.

In the embodiment illustrated the connector element 38 affords three passages extending therethrough in the direction of the length of the neck portion 30. With reference to FIG. 3, these comprise a first, relatively small diameter, passage 42, a second, larger-diameter passage 44 and a third passage 54. The passage 42 extends through spigots 46, 48 extending from the body of the connector element 38, respectively into the neck portion and to the exterior of the device. The passage 44 also extends through respective interior and exterior spigots 50, 52. The third passage 54 through the connector element has a tapering opening 56 in the connector element 38 and leads into an exterior spigot 58.

The passage 42 in the connector element 38 may provide for supply of a fluid e.g. oxygen, to the space between the wall elements of the device and hence to a wound to which the device is applied. A resiliently flexible tube 60 for supply of such fluid may be fitted on the spigot 48 (whose external surface is slightly tapered), and an appropriate length 62 of such tube may be fitted on the spigot 46 interior of the device to deliver such fluid to the wound. The passage 44 through the connector element 38 is of sufficient diameter to receive a flexible tube 64 such as for example a catheter, which could possibly be semi-permanently sutured into the wound, e.g. where a fistula is present. Passage 54 may provide for drainage of fluid from the wound, e.g. to a suitable positioned drainage bag, by way of a suitable flexible tube fitted on the exterior or into the interior of the spigot 58. A sealing sleeve 66 fits over the tube 64 and is of a flexible resilient material having a bore of stepped diameter, to fit sufficiently tightly to seal with the spigot 52 and the external surface of tube 64.

Referring now to FIG. 4 of the drawings, the individual thumbnails 4.1 to 4.21 thereof illustrate the mode of use of a wound management device in accordance with the invention. FIG. 4.1 shows a body part 70, e.g. the torso of a patient, having a wound 72 of irregular shape thereon. FIG. 4.2 shows the application of hydrocolloid paste to regions 74 of the skin surrounding the wound 72 where necessary, to fill any depressions or crevices in the surrounding skin to help ensure effective securement and sealing of the device thereto, while FIGS. 4.3 and 4.4 additionally show the application of some pieces of suitable adhesive tape 76 to part of the wound periphery. The next stage is to select a suitable size and shape of wound management device for application to the wound, the main criterion for such selection being that it should surround the wound and the adhesive part 36 of the device should extend sufficiently beyond the periphery of the wound for satisfactorily adhering to the surrounding skin. Having selected a suitable size and shape of device, a template 80 thereof is applied to the wound area, and the outline of the wound marked thereon by a suitable marker (FIG. 4.5, 4.6).

The marked template is then removed from the wound area, and a cut made around the marked wound outline thereon, to produce an opening therein whose shape corresponds to that of the wound.

The template 80 is then turned front-to-rear (FIG. 4.8, 4.9) and placed on the wound management device which is oriented with its rear sheet 14 uppermost, as shown in FIG. 4.10. The mirror-image of the wound periphery is marked on the adhesive element 36 of the device, and that outline is cut around as shown in FIG. 4.11, the result being (FIG. 4.12) a device whose wall element 14, and the adhesive area 36 and release sheet thereon, have an opening which, when applied to the wound, matches the size and shape of the wound.

Figure 414:
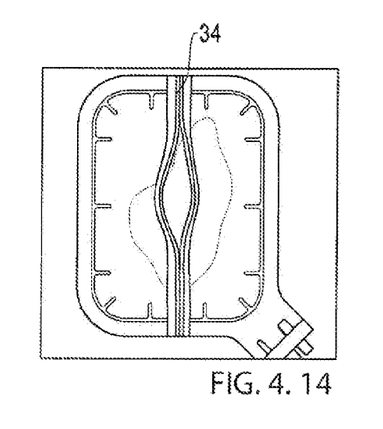
Figure 415:
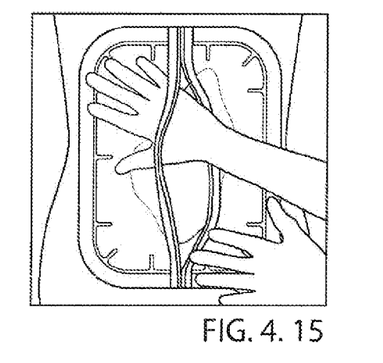
Figure 416:
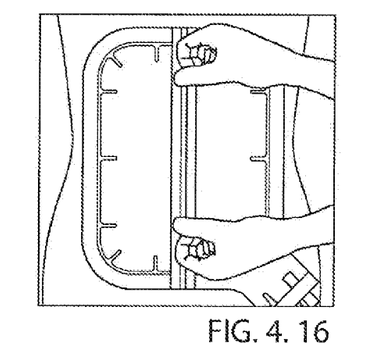

The release sheet can then be peeled off the adhesive element area 36 on the wall element 14 of the device, and the device carefully placed on the wound, to be secured adhesively to the skin surrounding the wound. As shown in FIGS. 4.14, 4.15 and 4.16, the access strip 34 may be opened to assist in applying the device to the wound area, after which the access strip can be closed.

Figure 417:
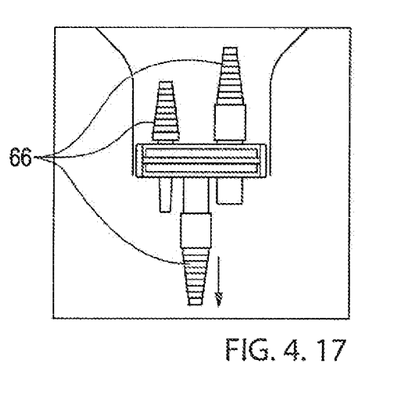
Figure 418:
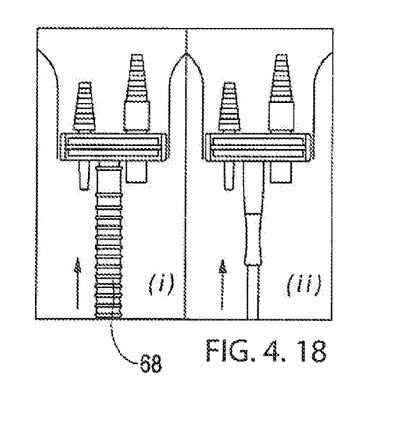

FIG. 4.17 shows sealing sleeves as 66 fitted on the spigots 46, 50, 58; while FIG. 4.18(i) shows a drainage tube 68 fitted by pushing onto the exterior of the spigot 58, and FIG. 4.18(ii) a different size drainage tube fitted into the interior of the spigot 58.

Figure 419:
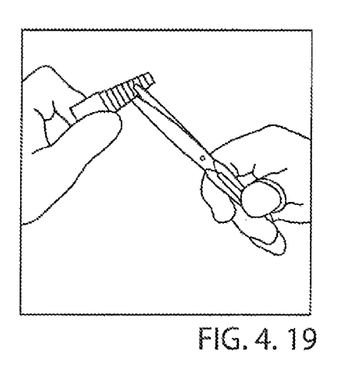
Figure 420:
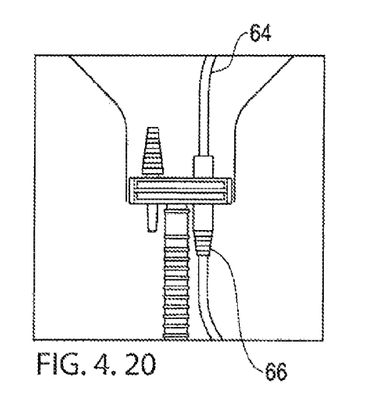
Figure 421:
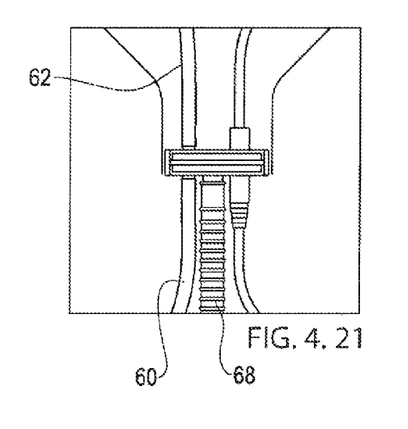

While the access strip is open, a catheter 64 may be positioned as required in the interior of the wound management device, in relation to the wound, and also a tubular element 62 may be so positioned. The sealing sleeve 66 may be appropriately cut to suit the diameter of the catheter 64 (FIG. 4.19).

From the above, it will be appreciated that the provision of the spigots on the connector element 38, and the provision of the access strip 34, together make the setting up of a wound management device in accordance with the invention a very convenient and quickly-executed procedure.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A wound management device comprising:
   first and second wall elements of flexible sheet material, the device being securable to skin around a wound site to define a space wherein the wound is accessible;
   the first and second wall elements being secured to one another to define a wound space therebetween, the first one of said wall elements being adapted for adhesive securement to skin around the wound site and being provided or being able to be provided with an opening for access between the wound site and the wound space between the wall elements;
   an openable and rescalable formation providing access to the wound space between the wall elements;
   a neck portion defined by at least one of the wall elements, wherein the neck portion includes a neck portion passage extending outwardly from the wound space; and
   a connector element secured to the neck portion and defining a distal end of the neck portion passage, wherein the connector element includes at least one passage for external communication with the wound space between the wall elements; and wherein the connector element further includes first and second spigots, each of which includes a spigot passage, for engagement by a member for fluid supply to or removal from the wound space, wherein the first spigot extends inwardly from the connector element into the neck portion passage toward the wound space and the second spigot extends outwardly from the connector element to the exterior of the device.

2. A wound management device according to claim 1 wherein the connector element comprises a body secured to the wall elements by being received and held between respective neck portions thereof.

3. A wound management device according to claim 1 wherein the connector element affords a plurality of passages extending through the connector element, more than one of such passages extending through a respective spigot.

4. A wound management device according to claim 3, wherein at least some of the plurality of passages are of different size from one another.

5. A wound management device according to claim 3 wherein one of the plurality of passages is for use as a drain passage.

6. A wound management device according to claim 5 wherein said drain passage is of larger size than the other of the plurality of passages.

7. A wound management device according to claim 5 wherein the drain passage extends through an exterior spigot.

8. A wound management device according to claim 1, wherein the second of said wall elements is provided with an openable and resealable formation providing access to the wound space between the wall elements.

9. A wound management device according to claim 8 wherein the openable and resealable formation comprises a zip-lock strip.

* * * * *